United States Patent [19]
Driver

[11] Patent Number: 5,349,848
[45] Date of Patent: Sep. 27, 1994

[54] CONSISTENCY MEASURING APPARATUS INCLUDING ELASTOMERIC MEMBER FOR IMPROVED RELIABILITY

[76] Inventor: Benjamin K. Driver, 6931 N. Century Blvd., Century, Fla. 32535

[21] Appl. No.: 15,528

[22] Filed: Feb. 9, 1993

[51] Int. Cl.⁵ .......................................... G01N 11/00
[52] U.S. Cl. ................... 73/54.28; 73/54.25; 73/54.26
[58] Field of Search ............ 73/54.23, 54.24, 54.25, 73/54.26, 54.28; 277/58, 212 C, 212 R, 205

[56] References Cited

U.S. PATENT DOCUMENTS

| | | | |
|---|---|---|---|
| 2,707,391 | 5/1955 | McSkimin | 73/54.24 |
| 4,062,226 | 12/1977 | Hietala | 73/54.23 |
| 4,757,708 | 7/1988 | Hietaranta | 73/54.23 |

FOREIGN PATENT DOCUMENTS

| | | | |
|---|---|---|---|
| 1608498 | 11/1990 | U.S.S.R. | 73/54.24 |

*Primary Examiner*—James C. Housel
*Assistant Examiner*—Laura E. Collins

[57] ABSTRACT

An elastomeric member is disposed in the enlarged opening of an on-line consistency measuring apparatus through which the blade carrier support shaft extends, and the elastomeric member is operative to prevent the solid-liquid slurry of a pulp stock slurry from interfering with the free movement of the carrier shaft or from contacting the "O" ring seal surrounding the shaft, thereby improving the reliability of the apparatus.

8 Claims, 2 Drawing Sheets

CONSISTENCY MEASURING APPARATUS INCLUDING ELASTOMERIC MEMBER FOR IMPROVED RELIABILITY

BACKGROUND OF THE INVENTION

The present invention relates to an on-line consistency measurement and control apparatus having improved reliability. The subject apparatus is employed for measuring the consistency of solid-liquid mixtures, i.e., flowing mediums having solids in suspension. More particularly, the subject apparatus is employed for measuring the consistency of non-Newtonian mixtures, that is, liquids wherein the shear rate and stress relation is non-linear, as in paper stock slurries. As referred to in the subject disclosure, consistency is defined as the ratio of weight of the solids to the total weight of the solids and liquid, for a given volume of the flowing medium.

In paper stock slurries, consistency is considered to be the percentage of fibers in the water. In the operation of certain industrial processes, it is important to be able to sense small variations in the consistency of a flowing slurry and to produce a corresponding output signal for transmission to suitable control apparatus or recording apparatus. Heretofore, various devices have been proposed for this purpose. Earlier devices were responsive essentially to the viscosity of the slurry, and thus were not well suited for use with non-Newtonian slurries. One type of earlier device for making consistency measurements of paper stock slurries was based on characteristics other than viscosity. For example, there are instruments designed to respond to shear forces apparently created by deforming the stock stream, and these instruments included a plurality of finger-like projections extending in the flow stream.

Another form of device for measuring the consistency of paper pulp stock is disclosed in U.S. Pat. No. 4,062,226 which issued to Veijo Hietala on Dec. 13, 1977 and is entitled "Device for Measuring Pulp Stock Consistency". The device of U.S. Pat. No. 4,062,226 includes a carrier shaft which extends transversely relative to the direction of flow of the paper stock slurry within a conduit, and the carrier shaft carries a sensing element extending from the shaft in the downstream direction of stock flow for effectively shearing the flowing stock and for responding to engagement with the stock for producing a torque capable of being measured for indicating consistency of the stock. The device of U.S. Pat. No. 4,062,226 includes a supporting structure that supports the carrier shaft and the sensing element carried thereby for adjustable movement upon an axis which is perpendicular to the carrier shaft and which also extends transversely with respect to the direction of stock flow. The sensing element has a surface situated in a plane that is oblique with respect to the carrier shaft so that, depending upon the direction and angle of adjustment of the carrier shaft and the sensing element carried thereby with respect to a neutral position where the oblique surface extends in the direction of stock flow, the stock will be deflected by the oblique surface to a given extent in a given direction producing in this way a torque of a direction and magnitude which depends upon the velocity of stock flow. To facilitate the angular movement and deflection of the carrier shaft, the carrier shaft is sealingly connected to the device for sensing angular movement of the shaft, and the shaft extends through an enlarged, generally conical opening in the monitoring device. The paper stock slurry flowing through the conduit consists of a mixture of wood pulp, pitch, water and chemicals, and it has been found that the pulp stock slurry enters the enlarged, generally conical area in the housing through which the shaft extends, and eventually wedges tight about the shaft thereby inhibiting the free movement of the shaft and thereby disabling the operation of the consistency monitor. In addition, the pulp stock eventually contacts the seal connection between the shaft and the housing of the measuring device, which seal connection is usually a conventional "O" ring. Eventually, the chemicals within the pulp stock destroy the integrity of the "O" ring, and this can also result in the consistency monitor being disabled.

In view of the above, it is an object of the subject invention to provide a new and improved consistency monitor including an encapsulating member for maintaining the flexibility of the carrier shaft and maintaining the integrity of the consistency monitor.

It is another object of the subject invention to increase the service life and reduce the amount of maintenance required for a consistency monitor, and to increase the accuracy and reliability of the consistency monitor over a greater period of time.

A further object of said invention is to eliminate "O" ring failure in a consistency monitor.

SUMMARY OF THE INVENTION

The subject invention is directed to a consistency measuring apparatus including an elastomeric member for improving reliability of the apparatus. The consistency measuring apparatus basically includes a blade member which is positioned within the conduit through which the paper stock slurry flows, and the blade member, in turn, is connected to a carrier shaft which extends transverse to the direction of flow of the paper stock slurry and is connected at its opposite end to an electronic measuring device which provides an output signal corresponding to the force applied to the carrier shaft by the blade member within the flow of the paper stock slurry. In order for the shaft to bend or deform in response to the forces applied thereto by variations in the consistency of the paper stock slurry as it impinges upon the blade member, the housing of the measuring device includes an enlarged opening through which the carrier shaft extends. By virtue of the enlarged opening, the end of the shaft which engages the blade member is free to deform or deflect in response to the forces applied to the blade member by the flow of the paper stock slurry. The carrier shaft is sealed to the measuring apparatus usually by means of a conventional "O" ring. Generally, the enlarged opening in the housing of the measuring device is configured as an inverted conical configuration, and in order to improve the reliability of the on-line consistency measurement and control device, the subject invention provides that a molten solution of elastomeric material be poured into the conical area of the apparatus in order to form a solid, flexible seal which surrounds the end of the carrier shaft which engages the blade member. At the same time, the elastomeric member surrounds the carrier shaft and in a manner so as to effectively insulate the "O" ring from the deleterious chemicals which are part of the paper stock slurry. Once the elastomeric member has solidified, the consistency meter is installed on the conduit and recalibrated. Thereafter, in use, the elastomeric member prevents the paper stock slurry which consists of wood pulp, pitch, water and chemicals from entering the enlarged conical area of the device, thereby preventing the paper stock slurry from wedging between the shaft and the housing which would result in disablement of the consistency monitor. In addition, the elastomeric member insulates the "O" ring which sealingly connects the carrier shaft to the housing of the measuring device, and thus prevents the chemicals within the paper stock slurry from affecting the integrity of the "O" ring.

The new and improved consistency measuring apparatus of the subject invention, with the elastomeric member, insures an interface seal between the paper stock slurry and the electronics within the measurement device, while also encapsulating the area around the flexible carrier shaft thereby maintaining the integrity of the measurement system. Encapsulation of the enlarged opening in the housing surrounding the shaft allows the carrier shaft to move as required in response to forces applied to the blade member, and maintains the measurement integrity of the consistency monitor, while increasing the service life of the monitor. Furthermore, the period of time between normal service life maintenance of the consistency measuring apparatus is prolonged, increased accuracy and reliability of the consistency measuring apparatus is obtained, and the possibility of "O" ring failure is greatly reduced.

DETAILED DESCRIPTION OF THE PREFERRED EMBODIMENT

Figure 1:
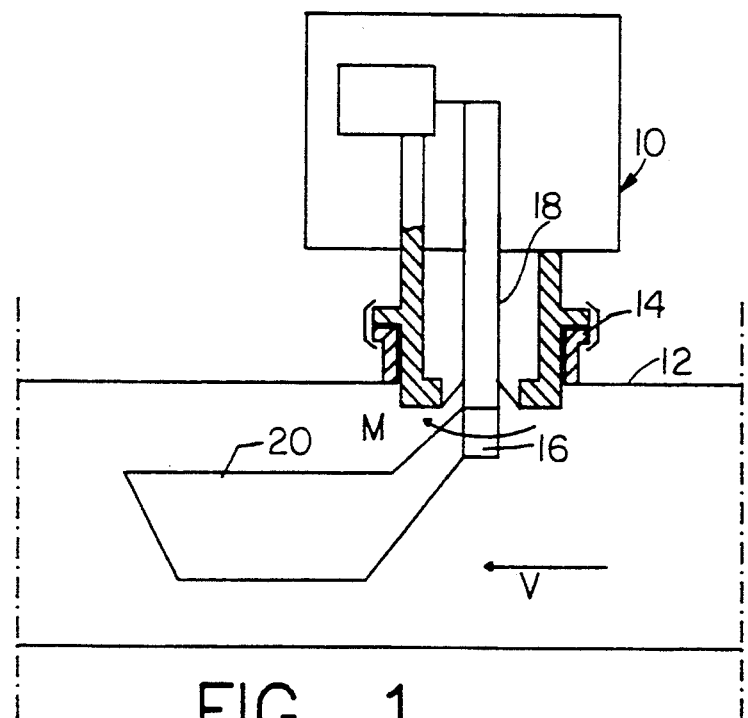
FIG. 1 is schematically represents a pulp stock consistency measuring according to the prior art.
Figure 2:
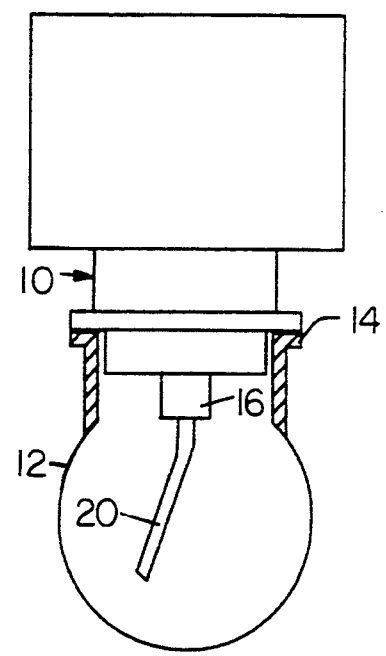
FIG. 2 schematically illustrates the prior art device of FIG. 1 as it appears when viewed in the direction of the stock flow with the plane of FIG. 2 being transverse to the direction of stock flow.
Figure 3:
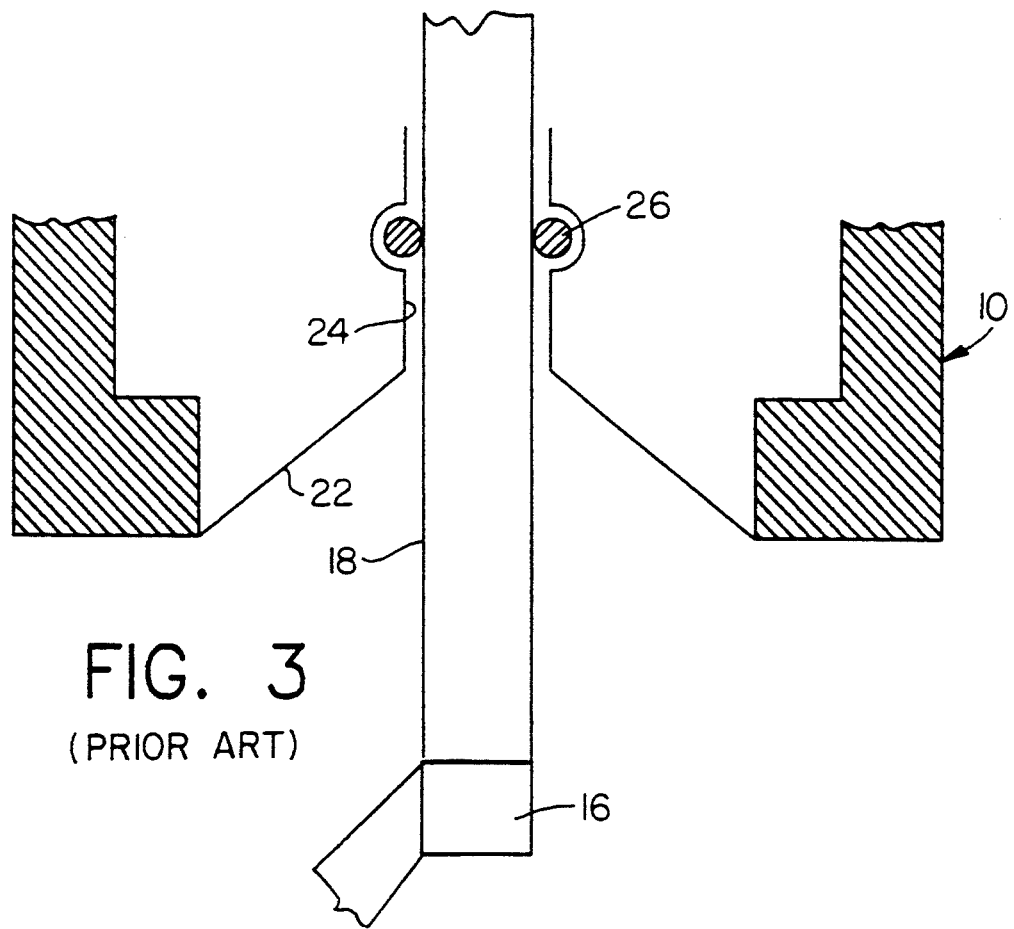
FIG. 3 is an enlarged detail of the interconnection between the carrier shaft and housing of the prior art pulp stock consistency measuring device of FIG. 1.

A prior art device for measuring pulp stock consistency is illustrated in FIGS. 1-3, and basically conforms to the disclosure of U.S. Pat. No. 4,062,226. The measuring device is generally designated by the numeral 10 and is connected to a conduit means 12 in the form of a suitable pipe or tube along which the paper stock flows in the direction designated by the arrow "v". For this purpose, the pipe 12 includes a flanged support means 14 for supporting the measuring device 10 for turning movement about an axis which extends transversely with respect to the direction "v" of stock flow. The support means 14 may be in the form of a circular tubular extension of the conduit means 12, so that the flanged support means 14 is of a cylindrical configuration and is circular in cross-section. The measuring device 10 has a portion extending freely through the tubular support means 14 and includes a flange which engages the upper surface of the flanged support means 14, as viewed in FIGS. 1 and 2, thereby enabling the entire device 10 to be capable of being turned about its longitudinal axis for adjustment relative to the pipe 12. A suitable exterior clamp forms part of the flanged support means 14 for releasably clamping the device 10 onto the pipe 12 in an adjusted angular position.

The measuring device 10 further includes a sensing means 16 which is carried by a flexible carrier shaft means 18 that extends transversely to the direction of flow, indicated by the arrow "v" in FIG. 1, of the pulp stock. Forming a portion of the sensing means 16 is an elongated blade 20 having the configuration of a paddle, shown most clearly in FIG. 1. The blade 20 extends into the body of the flowing pulp stock in a downstream direction from the carrier shaft means 18, and as shown in FIG. 2, the blade 20 is inclined at an oblique angle with respect to the axis of the shaft 18.

With the above described construction, the flowing pulp stock in the pipe 12 causes the application of a force to the blade 20 and, in turn, through the sensing means 16 and the flexible shaft 18 so as to generate a torque force, designated by the letter "M" in FIG. 1. Measurement of the torque force "M" is input to the electronics of the measuring device 10 and is used to calculate and control the consistency of the pulp stock flow in a well known manner. The sensing means 16 is directly carried by the shaft 18 which, in turn, is journalled in the body of the measuring device 10 so that through the flexible shaft 18 the sensing means 16 is journalled in the body of the measuring device 10.

As more particularly illustrated in FIG. 3, the prior art measuring device 10 includes an enlarged, generally inverted truncated conical opening defined by wall 22 leading to the generally cylindrical wall 24 within the measuring device 10. In order to seal the carrier shaft 18 to the wall 24, the measurement device 10 includes a conventional "O" ring seal 26.

With the construction of the conventional pulp stock consistency device 10 as illustrated in FIGS. 1-3, it is apparent that the pulp stock slurry which consists of wood pulp, pitch, water and chemicals can readily enter the inverted, truncated conical enlarged opening defined by the wall 22, and possibly flow into the journalled area of the carrier shaft means 18 in the region of the "O" ring 26 intermediate the shaft means 18 and the cylindrical wall 24. At such time, solid materials within the slurry, and more particularly the wood pulp and pitch may interfere with the free rotation and movement of the carrier shaft 18 thereby wedging tight the carrier shaft 18 and effectively disabling the monitor apparatus 10. At the same time, the chemical constituents of the pulp stock slurry engaging the "O" ring seal 26 could attack and possibly affect the integrity of the "O" ring seal 26, thereby also leading to the disablement of the monitor apparatus 10.

Figure 4:
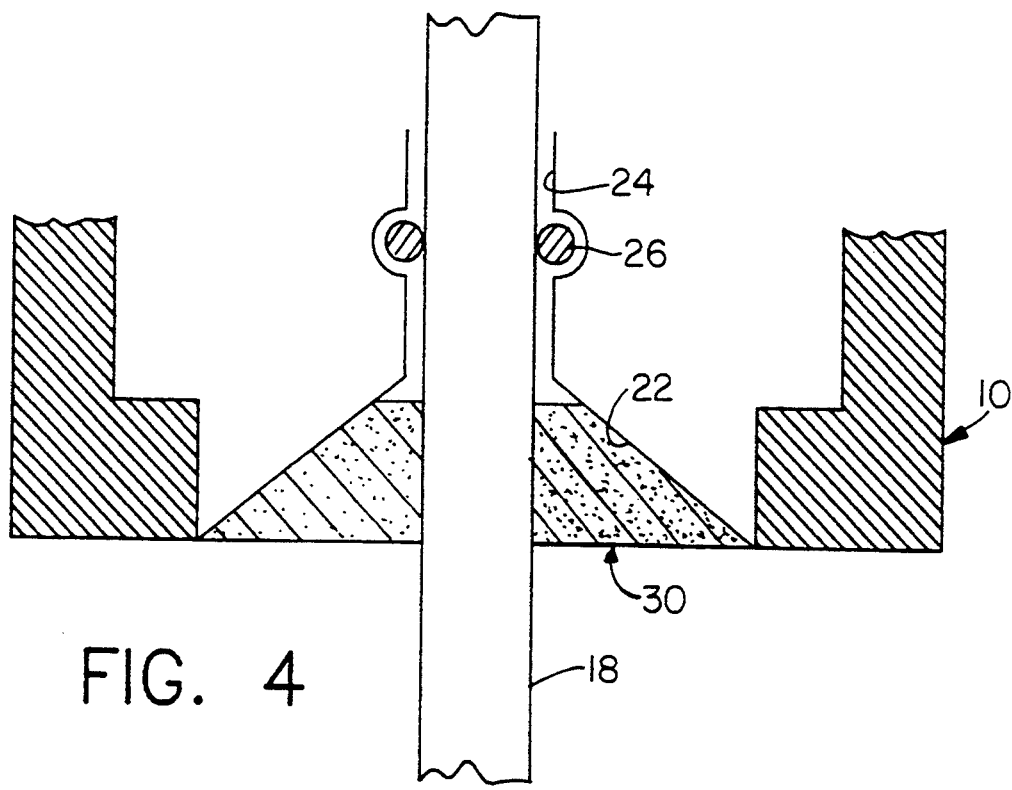
FIG. 4 is a view similar to FIG. 3 illustrating in detail the invention of the subject application.
Figure 5:
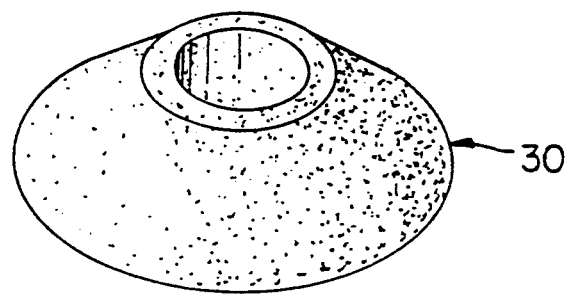
FIG. 5 is a schematic, perspective view of the elastomeric member of the subject invention.

The subject invention overcomes the above-mentioned problems, and the new and improved monitoring apparatus is more particularly illustrated in FIGS. 4 and 5. In the assembly of the improved consistency monitor, the housing is inverted prior to being installed on the pipe, and a molten solution of elastomeric material having properties similar to those of vulcanized natural rubber such as styrene butadiene copolymer, polychloroprene, butyl rubber, polyurethane rubber and silicone rubber is poured into the conical area defined by the wall 22. The preferred material is polyurethane resin compound. After the elastomeric solution sets, it turns into a solid, flexible member, designated by numeral 30 in FIGS. 4 and 5. Because of the elastomeric characteristics of member 30, when the monitor 10 is installed in a pipe, the pulp stock slurry is prevented from entering the inverted truncated conical area defined by wall 22, and at the same time the slurry is prevented from contacting the "O" ring seal 26. At the same time, because of the elastomeric characteristics of the elastomeric member 30, shaft 18 is capable of movement or deflection in response to forces being applied by the paper stock slurry against the blade 20. The opposite end of the carrier shaft 18 is connected to the electronic measuring circuitry (not shown) within the monitor 10 in order to detect the consistency of the paper stock slurry.

With the elastomeric member 30 in place, the life span of the monitor 10 is increased, with longer term accuracy and less down time for maintenance and cleaning. More particularly, the new and improved on-line consistency monitor and control apparatus 10 including the elastomeric member 30 functions to provide an interface seal between those mechanical portions of the blade 20, sensing means 16 and shaft 18 and the delicate electronics within the monitor, while at the same time encapsulating the inverted truncated conical area within the housing surrounding shaft 18 in a manner which ensures the free flexibility of said mechanical portions of the system to maintain measurement integrity of the system. Furthermore, encapsulation of the truncated conical area around shaft 18 with the flexible elastomeric member 30 allows the shaft 18 to move freely for maintaining measurement integrity and increased service life of the on-line consistency monitor.

While the invention has been described with respect to a preferred embodiment, it is apparent that various changes can be made without departing from the spirit and the scope of the invention as defined by the appended claims.

What is claimed is:

1. An apparatus for measuring the consistency of a flowing solid-liquid mixture comprising:
    a blade member positioned within a flowing solid-liquid mixture;
    carrier shaft means extending transversely with respect to the direction of flow of the mixture, said carrier shaft means being connected at one end thereof to the blade member;
    a measuring device coupled to the other end of said carrier shaft means by the blade member for producing an output signal corresponding to applied force; said measuring device including a housing having an enlarged inverted truncated conical opening through which said carrier shaft means extends, said carrier shaft means in sealing connection to the housing; and
    an elastomeric member disposed in said enlarged opening of said housing substantially filling the same and surrounding a portion of the carrier shaft means extending through said opening thereby preventing solid liquid mixture from contacting said sealing connection provided between said carrier shaft means and the housing, and preventing said solid liquid mixture from interfering with free movement of said carrier shaft means in response to force applied thereto by the blade member.

2. An apparatus for measuring the consistency of a flowing solid-liquid mixture as in claim 1 wherein said elastomeric member is made of styrene butadiene copolymer, polychloroprene, butyl rubber, polyurethane rubber or silicone rubber.

3. An apparatus for measuring the consistency of a flowing solid-liquid mixture as in claim 1 wherein said elastomeric member is made of a polyurethane resin compound.

4. An apparatus for measuring the consistency of a flowing solid-liquid mixture as in claim 1 wherein the sealing connection between said carrier shaft means and the housing is an "O" ring.

5. An apparatus for the on-line measurement of the consistency of a pulp stock slurry consisting of a mixture of wood pulp, pitch, water and chemicals comprising:
    a blade member positioned within a flowing pulp stock slurry;
    a carrier shaft extending transversely with respect to the direction of flow of said pulp stock slurry, said carrier shaft being connected at one end thereof to said blade member;
    a measurement device coupled to the other end of said carrier shaft and including means responsive to forces applied to said carrier shaft by the blade men, her for producing an output signal corresponding to the free movement of said carrier shaft means in response to forces applied thereto by the blade member; said measurement device including a housing having an enlarged opening of generally inverted truncated conical configuration, said carrier shaft in sealing connection to said housing; and
    an elastomeric member disposed in and corresponding to the configuration of said enlarged inverted truncated conical opening of said housing and surrounding a portion of the carrier shaft extending through said opening thereby preventing the pulp stock slurry from contacting said sealing connection provided between said carrier shaft and the housing, and preventing said pulp stock slurry from interfering with free movement of said carrier shaft in response to forces applied thereto by the blade member.

6. An apparatus for the on-line measurement of the consistency of a pulp stock slurry consisting of a mixture of wood pulp, pitch, water and chemicals as in claim 5 wherein said sealing connection between said carrier shaft and the housing is an "O" ring.

7. An apparatus for the online measurement of the consistency of a pulp stock slurry consisting of a mixture of wood pulp, pitch, water and chemicals as in claim 5 wherein said elastomeric member is made of styrene butadiene copolymer, polychloroprene, butyl rubber, polyurethane rubber or silicone rubber.

8. An apparatus for the on-line measurement of the consistency of a pulp stock slurry consisting of a mixture of wood pulp, pitch, water and chemicals as in claim 5 wherein said elastomeric member is made of a polyurethane resin compound material.

* * * * *